United States Patent [19]

Isa et al.

[11] 3,953,361

[45] Apr. 27, 1976

[54] METHOD OF MANUFACTURING GRANULAR SOLID CATALYST

[75] Inventors: Hiroshi Isa; Toshiyuki Ukigai, both of Yachiyo; Anry Tominaga, Tokyo; Ryozo Taniyasu, Narashino; Masuzo Nagayama, Tokyo, all of Japan

[73] Assignee: Lion Fat & Oil Co., Ltd., Tokyo, Japan

[22] Filed: Nov. 27, 1974

[21] Appl. No.: 527,644

[30] Foreign Application Priority Data
Dec. 14, 1973 Japan.............................. 48-138784

[52] U.S. Cl............................................ 252/429 R
[51] Int. Cl.²......................................... B01J 31/02
[58] Field of Search ................................ 252/429 R

[56] References Cited

UNITED STATES PATENTS

| | | | |
|---|---|---|---|
| 2,085,535 | 6/1937 | Langedijk........................ | 252/429 R |
| 2,422,798 | 6/1947 | Pines................................ | 252/429 R |
| 2,697,694 | 12/1954 | Shalit................................ | 252/429 R |

*Primary Examiner*—Helen M. McCarthy
*Attorney, Agent, or Firm*—Woodhams, Blanchard and Flynn

[57] ABSTRACT

A method of manufacturing granular solid catalyst, comprising the process of mixing more than 1 mole of olefin and 1.0 – 1.2 mole of ketone having 4 or more carbon atoms relative to 1 mole of aluminum halide and effecting reaction at a temperature of more than 60°C.

12 Claims, No Drawings

METHOD OF MANUFACTURING GRANULAR SOLID CATALYST

BACKGROUND OF THE INVENTION a. Field of the Invention

The present invention relates to a method of manufacturing a granular solid catalyst useful for polymerizing olefin and like purposes.

b. Description of the Prior Art

The art of utilizing Lewis acids like aluminum chloride for polymerizing olefins has been known for a long time, but inasmuch as such conventional catalysts are soluble in olefins, they are hard to separate after termination of the reaction, and in the present circumstances, they must be removed through decomposition by the use of aqueous alkali, aqueous ammonia, adsorbent and the like. Accordingly, these catalysts are difficult to reuse and unfit for use in reactions effected by employing a fixed bed or a fluid bed.

With a view to overcoming such defects, there have been made various studies on complex catalysts consisting of aluminum chloride and polar organic compounds: for instance, Japanese Patent Publication No. 3840/1969 has disclosed the method of polymerizing olefin by the use of a catalyst prepared by dissolving excess aluminum chloride in a complex consisting of aluminum chloride and ethyl acetate at the ratio of 1:1, which renders it easy to separate the catalyst, and U.S. Pat. No. 2,697,694 has proposed a catalyst prepared by dissolving excess aluminum chloride in a complex consisting of aluminum chloride and acetone at the ratio of 1:1, said catalyst being reported to have the same effect as that in the preceding catalyst.

However, these complexes have no more than the function as a solvent to dissolve aluminum chloride, and the polymerization reaction per se is effected by virtue of the excess dissolved aluminum chloride, so that, upon completion of the reaction, the same treatment as in the case of the ordinary catalysts consisting exclusively of aluminum chloride is required. Further, in the case where these complexes are to be used repeatedly, it is necessary to effect the next reaction by replenishing the aluminum chloride consumed in the previous reaction.

Therefore, the known methods employing these complexes are no more than a method wherein a solvent to dissolve aluminum chloride is being circulated, and the catalyst not only becomes unfit for reuse as it is after it is once used, but also is inapplicable to a continuous reaction employing a fixed bed or a fluid bed.

SUMMARY OF THE INVENTION

The present invention is to provide a method of manufacturing a granular solid catalyst, which catalyst can be repeatedly used for effecting reactions such as polymerization of olefins and the like and is suitable for use in the continuous reaction employing the fixed bed or the fluid bed. And, the present invention is characterized by the process of mixing more than 1 mole of olefin and 1.0 – 1.2 mole of ketone having 4 or more carbon atoms relative to 1 mole of aluminum halide and effecting reaction at a temperature of more than 60° C.

General complexes consisting of aluminum halide and a polar organic compound such as ester, ketone, ether, etc. at the ratio of 1:1 are said to be incapable of catalytic action, and in fact, an active granular catalyst cannot be obtained by mere heating of ketone together with aluminum chloride. Further, even in the presence of olefin, in the case where the temperature for activating thereof is too low or the amount of ketone is too high, an active granular catalyst cannot be obtained. That is, an active granular catalyst can be obtained only when olefin, ketone having 4 or more carbon atoms and aluminum chloride are compounded at a mixing ratio in a very limited range and activated by applying a relatively high temperature. Accordingly, it is hardly considered that this active catalyst is a mere complex of ketone and aluminum halide. It seems that the catalyst having a peculiar structure under the present invention is produced subject to compounding aluminum halide, olefin and ketone having 4 or more carbon atoms at a specific ratio and effecting reaction at a fixed temperature for activation as set forth above. Though the structure of the catalyst of the present invention is yet to be clarified, judging from the results of measurements by means of IR as well as NMR which indicated that alkyl carbon was scarcely present therein, there seems to have been formed a catalyst ingredient having some active points, such as in the case of the inorganic solid acid catalyst, through some complicated reaction processes. And, it is presumed that the olefin is polymerized at said active points and then separates, thereby producing a catalyst which can be reused repeatedly.

As the applicable aluminum halide, there are, for instance, aluminum fluoride, aluminum chloride, aluminum bromide, etc. of which aluminum chloride is particularly desirable. As the applicable olefin, straight-chain or branched-chain α - or inner-olefins are effective: to give examples, there are propylene, isobutene, hexene-1, octene-2, tridecene-1, octadecene-2 and their mixtures. Among the foregoing olefins, from the view point of the activity of catalyst, α- or inner olefins having more than 6 carbon atoms are particularly desirable. The ketone for use in the present invention means chain-structure ketone or cylic ketone having 4 or more carbon atoms, including diketone and keto acid ester too. To give instances of applicable ketones, there are methyl ethyl ketone, diethyl ketone, diisobutyl ketone, dioctyl ketone, acetyl acetone, cyclohexanone, pyruvic acid ester and their analogues. Acetone having 3 carbon atoms is ineffective to produce a catalyst, and is therefore undesirable.

The above described aluminum halide, olefin and ketone should be compounded at a fixed mixing ratio. The molar ratio of aluminum halide to olefin suffices to be more than 1 mole of olefin relative to 1 mole of aluminum halide, but the highest activity is realized when olefin is in the range of 5 – 20 moles. The molar ratio of aluminum halide to ketone is required to be 1.0 – 1.20 mole of ketone relative to 1 mole of aluminum halide: in the case where aluminum halide is present in excess, the resulting catalyst comes to dissolve in polymer, thereby necessitating after-treatment, while in the case where ketone is more than 1.2 mole, the catalyst fails to be active. The most desirable ratio is 1.02 – 1.10 mole of ketone relative to 1 mole of aluminum halide. The temperature at the time of manufacturing the catalyst also constitutes an important factor of the present invention, and in order to obtain a granular catalyst under the present invention, a temperature of more than 60°C at the least is required. In order to obtain a catalyst capable of demonstrating the highest catalytic activity, the temperature for reaction at the time of manufacturing thereof is in the range of 100° – 150° C.

The catalyst of the present invention is obtained through the process comprising dissolving aluminum halide in ketone completely, subsequently adding olefin and raising the temperature of the resulting mixture, and separating granular solid which precipitates 1 – 2 hours thereafter. The diameter of the thus obtained granular catalyst — though it depends on the molar ratio of the applied ingredients and the temperature for reaction — is almost in the range of 0.1 – 2 mm. In the case of effecting polymerization of olefins and the like, it is also possible to perform the manufacture of catalyst together with the polymerization reaction within one and the same system upon adding the starting olefin simultaneously with the other ingredients. The characteristic feature of the present invention lies in that it renders it possible to manufacture a granular solid catalyst useful for polymerization reaction of olefin and the like from aluminum halide, ketone and olefin, and the fact that the catalyst system in the present invention consists of granular solid is indicative of the advantages such that the catalyst can be easily separated by merely leaving it standing still upon completion of the reaction and it can be reused for the next reaction as it is. This is evident from the fact that, when the present catalyst was employed for polymerization of α-olefin having 8 carbon atoms, it was possible to effect the reaction as many as 6 times without causing any practical decrease of yield.

Because of the foregoing advantages, the present catalyst renders it possible to perform continuous reaction employing either a fixed bed or a fluid bed, which has hitherto been considered almost impossible to perform by means of the aluminum chloride type catalyst, and accordingly, it has become possible to manufacture polymers of olefins useful for lubricant and so forth by the use of large-scale apparatuses. Besides, in the case where the polymerization of the olefin is performed by the use of a granular catalyst under the present invention, the catalyst requires no such troublesome process as decomposition of catalyst after completion of the reaction like in the case of the conventional aluminum halide type catalyst, but can be directly served for distillation or hydrogenation. Further, the present granular catalyst can be used also for the alkylation reaction, hydration reaction and isomerization reaction of olefins in addition to the polymerization reaction of olefin.

DESCRIPTION OF THE PREFERRED EMBODIMENTS

Comparative Example 1.

When reaction was effected for 2 hours by raising the temperature up to 100° C after placing 10g of methyl ethyl ketone, 22g of aluminum chloride (the molar ratio of aluminum chloride to methyl ethyl ketone = 1:0.82) and 92g of octene-1 in a 0.3l glass autoclave with stirrer, there was formed a mud-like catalyst layer, but no granular solid catalyst was obtained.

Comparative Example 2.

When reaction was effected for 2 hours by raising the temperature up to 120° C after placing 34g of methyl ethyl ketone, 22g of aluminum chloride (the molar ratio of aluminum chloride to methyl ethyl ketone = 1:1.30) and 92g of octene-1 in the same autoclave as in Comparative Example 1, there was formed a mud-like catalyst layer, but no glanular solid catalyst was obtained.

Comparative Example 3.

When reaction was effected for 2 hours at a temperature of 40° C after placing 6.8g of methyl ethyl ketone, 12g of aluminum chloride (the molar ratio of aluminum chloride to methyl ethyl ketone = 1:1.02) and 92g of octene-1 in the same glass autoclave as in Comparative Example 1, there was formed no catalyst layer.

Comparative Example 4.

When reaction was effected for 2 hours by raising the temperature up to 120° C after placing 8.2g of acetone having 3 carbon atoms, 18g of aluminum chloride and 92g of octene-1 in the same glass autoclave as in Comparative Example 1, there was formed a mud-like catalyst layer, but no granular solid catalyst was obtained.

EXAMPLE 1.

When reaction was effected for 2 hours by raising the temperature up to 100° C after placing 6.8g of methyl ethyl ketone, 12g of aluminum chloride (the molar ratio of aluminum chloride to methyl ethyl ketone = 1:1.02) and 92g of octene-1, there could be separated a catalyst layer consisting of grains having a mean diameter of about 0.5 – 1 mm. Upon stocking the thus obtained granular catalyst in its entirety in a 1l glass autoclave and adding 600g of octene-1 thereto, reaction was effected for 5 hours by raising the temperature up to 120° C. After completion of the reaction, the catalyst was separated by setting, and the resulting upper layer was subjected to distillation in that condition, whereby the unreacted olefin and dimer of olefin were removed. The yield of the polymerized oil was 84%, and the viscosity of said polymerized oil at 100° F was 29 centistokes. Meanwhile, when reaction was effected in the same way as above upon stocking the granular catalyst obtained through separation by setting in said autoclave once more, the yield of the polymerized oil was 80% and the viscosity thereof at 100° F was 27 centistokes. Further, when the same reaction as above was effected again by applying the hereby separated catalyst, the yield of the resulting polymerized oil was 74% and the viscosity thereof at 100° F was 32 centistokes. As verified by the foregoing experiments, the granular catalyst obtained in the present example can be used repeatedly.

Furthermore, upon charging 50g of the granular catalyst obtained in the present example in a cylindrical reactor of 4 cm in diameter and 40 cm in height, polymerization reaction was effected by introducing octene-1 into said reactor through the lower part thereof at the speed of 2 cc per minutes after heating it up to 120° C. When the reaction mixture flowed out of the upper part of the reactor was treated by applying the foregoing test procedure of repeated use, the yield of the resulting polymerized oil was 82% and the viscosity thereof at 100° F was 30 centistokes. When this reactor was operated continuously for 24 hours and a sample obtained thereafter was analyzed, both the yield and the viscosity of polymerized oil showed little change. This proves that the granular catalyst obtained in the present example is servable for continuous reaction.

EXAMPLE 2.

When reaction was effected under the same conditions as in Example 1 except for replacing methyl ethyl ketone with 9.3g of cyclohexanone, there was separated a catalyst layer consisting of grains having a mean diameter of about 0.2 – 0.5 mm. When polymerization of olefin was performed by the use of the thus obtained granular solid catalyst and by applying the same procedure as in the test by repeated use in Example 1, the yield of the resulting polymerized oil was 79% and the viscosity thereof at 100° F was 62 centistokes. And, this yield and viscosity showed little change even after the reaction was repeated 3 times.

EXAMPLE 3.

When reaction was effected under the same conditions as in Example 1 except for replacing octene-1 with dodecene-1, there was obtained a granular catalyst having a mean diameter of about 0.5 – 1.0 mm. When polymerization of dodecene-1 was performed by the use of this catalyst and by applying the same procedure as in the test by repeated use in Example 1, the yield of the resulting polymerized oil was 75% and the viscosity thereof at 100° F was 42 centistokes. And, this yield and viscosity showed little change even after the reaction was repeated 4 times.

EXAMPLE 4.

When reaction was effected under the same conditions as in Example 1 except for replacing octene-1 with butene-1, there was obtained a granular catalyst having a mean diameter of about 0.5 – 1.0 mm. When polymerization of butene-1 was performed by the use of this catalyst and by applying the same procedure as in the test by repeated use in Example 1, the yield of the resulting polymerized oil was 55% and the viscosity thereof at 100° F was 28 centistokes.

EXAMPLE 5.

When reaction was effected under the same conditions as in Example 1 except for changing the molar ratio of aluminum chloride to methyl ethyl ketone to be 1:1.2, there was separated a catalyst layer consisting of grains having a mean diameter of about 0.1 mm. When polymerization of olefin was performed by the use of the thus obtained granular solid catalyst and by applying the same procedure as in the test by repeated use in Example 1, the yield of the resulting polymerized oil was 70% and the viscosity thereof at 100° F was 88 centistokes. And, after the reaction was repeated 3 times, said yield was 62%.

What is claimed is:

1. A process for preparing a granular solid catalyst, which comprises: reacting at a temperature of more than 60° C, a reaction mixture consisting essentially of
   a. an $\alpha$-olefin or internal olefin having 3 or more carbon atoms, or mixtures thereof,
   b. an aluminum halide, and
   c. a ketone selected from the group consisting of methyl ethyl ketone, diethyl ketone, diisobutyl ketone, dioctyl ketone, acetyl acetone, cyclohexanone and pyruvic acid esters wherein the reaction mixture contains from 1.0 to 1.20 moles of said ketone (c) and more than one mole of said olefin (a), per one mole of said aluminum halide (b), until there precipitates a granular solid catalyst having a particle size in the range of about 0.1 to 2.0 mm.

2. A process according to claim 1, wherein said olefin has more than 6 carbon atoms.

3. A process according to claim 1, wherein the reaction mixture contains 5 – 20 moles of olefin per one mole of aluminum halide.

4. A process according to claim 1, wherein the reaction mixture contains 1.02 – 1.10 mole of ketone per one mole of aluminum halide.

5. A process according to claim 1, wherein the reaction temperature is in the range of 100° – 150° C.

6. A process according to claim 1, wherein the olefin is added after completely dissolving the aluminum halide in the ketone and then the temperature is raised to the reaction temperature.

7. A process according to claim 1, wherein aluminum chloride, olefin and ketone are mixed simultaneously.

8. A process as claimed in claim 1 in which said olefin is selected from the group consisting of propylene, isobutene, butene-1, hexene-1, octene-1, octene-2, dodecene-1, tridecene-1 and octadecene-2, and said aluminum halide is aluminum chloride.

9. A process as claimed in claim 8 in which said ketone is methyl ethyl ketone.

10. A process as claimed in claim 8 in which said ketone is cyclohexanone.

11. A process as claimed in claim 9 in which said olefin is selected from the group consisting of octene-1, dodecene-1 and butene-1.

12. A process as claimed in claim 10 in which said olefin is octene-1.

* * * * *